(12) United States Patent
Joziak et al.

(10) Patent No.: US 6,346,235 B1
(45) Date of Patent: Feb. 12, 2002

(54) DUAL COMPONENT DENTIFRICE COMPOSITION FOR FLUORIDATING TEETH

(75) Inventors: Marilou T. Joziak, South River; Edward A. Tavss, Kendall Park; Steven W. Fisher, Middlesex; Robert J. Gambogi, Belle Mead, all of NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 09/519,507

(22) Filed: Mar. 6, 2000

Related U.S. Application Data

(63) Continuation-in-part of application No. 09/067,819, filed on Apr. 28, 1998.

(51) Int. Cl.$^7$ ............... A61K 7/16; A61K 7/18
(52) U.S. Cl. ............... 424/52; 424/49
(58) Field of Search .............. 424/49–58

(56) References Cited

U.S. PATENT DOCUMENTS

| | | | | |
|---|---|---|---|---|
| 3,937,804 A | * | 2/1976 | Delaney et al. | 424/52 |
| 4,098,435 A | * | 7/1978 | Weyn | 222/94 |
| 4,160,022 A | * | 7/1979 | Delaney et al. | 424/52 |
| 4,211,341 A | * | 7/1980 | Weyn | 222/94 |
| 4,487,757 A | * | 12/1984 | Kiozpeoplou | 424/49 |
| 4,545,979 A | * | 10/1985 | Ambikh et al. | 424/52 |
| 4,687,663 A | * | 8/1987 | Schaeffer | 424/52 |
| 5,215,740 A | * | 6/1993 | Domke et al. | 424/52 |
| 5,855,871 A | * | 1/1999 | Masters et al. | 424/49 |
| 6,123,926 A | * | 9/2000 | Parikh et al. | 424/52 |
| 6,180,089 B1 | * | 1/2001 | Gambogi et al. | 424/52 |

OTHER PUBLICATIONS

Prencipe et al Chem Tech "Squeezing Out a Better Toothpaste" (cited in (H), Dec. 1995.*

* cited by examiner

*Primary Examiner*—Shep K. Rose
(74) *Attorney, Agent, or Firm*—Paul Shapiro

(57) ABSTRACT

A method is disclosed for enhancing fluoride availability using an acidulated two component dentifrice system in which the first component contains sodium fluoride and a silica abrasive in an alkaline environment and the second component contains an acid, a phosphate ion source, and a silica abrasive.

12 Claims, No Drawings

DUAL COMPONENT DENTIFRICE COMPOSITION FOR FLUORIDATING TEETH

This is a continuation-in-part of pending prior application Ser. No. 9/067,819, filed Apr. 28, 1998, which application is now pending.

BACKGROUND OF THE INVENTION

1. Field of the Invention

This invention is directed to a dentifrice composition containing acidulated fluoride compounds effective as anticaries agents and more particularly to an acidulated phosphate fluoride dual component dentifrice composition for fluoridating teeth.

2. The Prior Art

It has long been known to include fluoride containing compounds in dentifrices as anticaries agents, and it has been established that these compounds are effective to reduce the incidence of dental caries. Fluoride compounds which are deemed to be the most effective are sodium fluoride, sodium monoflurophosphate and stannous fluoride. The fluoride compounds are effective mainly due to the fluoride ions which improve the acid resistance of tooth enamel and accelerate remineralization (i.e. recalcification) of decayed teeth in their early stage when the decalcification has proceeded only slightly. The effect of improving the acid resistance of the enamel is believed to be due to the fact that the fluoride ions are incorporated into a crystal lattice of hydroxyapatite which is the main constituent of tooth enamel or, in other words, fluoride ions partially fluoridate hydroxyapatite and simultaneously repair the lattice irregularities.

The effectiveness of fluoride treatment in providing acid resistance to tooth enamel is dependent upon the amount of fluoride ion which is available for deposition on the enamel being treated. Also, using phosphate buffered NaF, the incorporation of fluoride as $CaF_2$ into dental enamel is facilitated at lower pH levels which increase enamel solubility. Prencipe et al., *Colloid & Surface Chemistry*, $4^{th}$ *Chemical Congress of America*, New York (Aug. 25–30, 1991). It is, therefore, desirable to formulate an acidulated phosphate fluoride dentifrice to enhance fluoride deposition onto and uptake into the tooth enamel.

Acidulated phosphate fluoride is disclosed in U.S. Pat. Nos. 4,080,440 and 5,603,992 as delivered in a dual component dentifrice comprised of a separately housed first acidic component containing a fluoride salt such as NaF, which with a second separately housed cationic calcium ion containing component, forms the two component dentifrice for tooth remineralization. While these two separately housed component formulations avoid any reactions between ingredients within the first and second components during storage, upon application to the teeth the fluoride salt will begin to react with the cationic calcium ion, reducing the availability of the fluoride for fluoridation of the teeth. Further, a reaction occurs during storage within the first component itself, between the acid, the sodium fluoride and the silica abrasive therein, reducing the bioavailability of the fluoride ion. The amorphous silica abrasive ingredient generally used in dentifrices is one of the most chemically inert abrasives available, however, the negatively charged oxygen atoms of the silica are protonated in the acid environment, and the resulting hydroxyl (OH) moieties hydrogen bond to the available fluoride ions released from the sodium fluoride. This fluoride-OH bond occurs in the acidulated phosphate fluoride silica abrasive systems disclosed in prior art U.S. Pat. Nos. 4,080,440, and 5,603,922 whereby, the availability of the fluoride ions present in the dentifrice to fluoridate the enamel upon application thereto is significantly reduced. The magnitude of this reduction in available fluoride is hereinafter demonstrated.

Thus, there is a clear need to formulate a stable, acidulated phosphate fluoride dentifrice, having the maximum deliverable fluoride.

SUMMARY OF THE INVENTION

In accordance with the present invention there is provided a method for the fluoridation of tooth enamel using a multicomponent dentifrice comprised of two separately housed, semi-solid aqueous components; the first component containing sodium fluoride as a source of fluoride ions, in an orally acceptable vehicle having a pH of at least about 7.5 and, the second component which is fluoride free containing both a source of phosphate ions and an acid to provide a pH of from about 2.5 to about 5.0, in an orally acceptable vehicle; each component containing a siliceous abrasive and each component being free of any cationic calcium ion containing component, such as water soluble calcium salts, whereby upon mixing of the components, a mixture having a pH of from about 4.0 to about 6.0 is formed, whereby upon application of the mixture to the teeth, the availability of fluoride ions is enhanced.

There has been no recognition in the prior art of the significant loss of fluoride availability during extended periods of storage, resulting from the interaction of generally inert silica abrasives, with sodium fluoride, when NaF is present as the fluoride source in dentifrices having an acid environment. In accordance with the present invention, as will be further demonstrated herein, the enhanced fluoride availability resulting from separating the acid and the fluoride in separate dentifrice components, each containing a silica abrasive, is unexpected and significant.

DESCRIPTION OF THE PREFERRED EMBODIMENTS

In use, the components of the two component dentifrice of the present invention comprise a first sodium fluoride and silica abrasive containing dentifrice component, and a second acid and silica abrasive containing dentifrice component; these two components are preferably combined in approximately equal weight proportions, so that about one-half of the concentration of any particular ingredient within either component will be present when the components are combined and applied to the teeth, as by brushing. Both components are formulated to provide similar apparent physical characteristics, so that the two components are simultaneously delivered in the desired predetermined amounts by extrusion from a multicompartmented tube or pump device.

Dentifrice Vehicle Common to Both Components

In the preparation of the individual dentifrice components of the present invention, the respective sodium fluoride or acid is incorporated within a dentifrice vehicle suitable for use in the oral cavity, which contains water, humectant, surfactant and a polishing agent or abrasive. The humectant is generally a mixture of humectants, such as glycerol, sorbitol and polyethylene glycol of a molecular weight in the range of 200–1000, but other mixtures of humectants and single humectants may also be employed. The humectant content within each of the two components is in the range about of 20% to about 50% by weight and preferably about 30 to about 45% by weight. The water content is from about 20% to about 45%, and preferably about 30 to about 42% by weight.

Surface active agents or surfactants may be incorporated in the vehicle of the individual components of the present invention, as an ingredient to aid in the thorough dispersion of the dentifrice throughout the oral cavity when applied thereto, as well as, to improve the dentifrice's cosmetic acceptability and the foaming properties. Anionic surfactants are preferred in the first, sodium fluoride, containing component. Nonionic surfactants are preferred in the second, acid, containing component.

Examples of suitable anionic surfactants for use in the first component of the present invention include water soluble salts of the higher alkyl sulfates or sulfoacetate, such as sodium lauryl sulfate, sodium lauryl sulfoacetate or other suitable alkyl sulfates or sulfoacetates having 8 to 18 carbon atoms in the alkyl group; water soluble salts of sulfonated monoglycerides of higher fatty acids, such as sodium coconut monoglyceride sulfonate or other suitable sulfonated monoglyceride of a fatty acid of 10 to 18 carbon atoms; sodium lauryl phosphate salts of amides of higher fatty acid, e.g., 12 to 16 carbon atom acids, with lower aliphatic amino acids, e.g., taurine or sarcosine, or other amino acid of 2 to 6 carbon atoms, such as sodium-N-methyl-N-palmitoyl tauride, sodium N-lauroyl-, N-myristoyl- and N-palmitoyl sarcosinates; water soluble salts of the esters of such fatty acids with isethionic acid or with glycerol monosulfate, such as the sodium salt of monosulfated monoglyceride of hydrogenated coconut oil fatty acids; water soluble salts of olefin sulfonates, e.g., alkene sulfonates or hydroxyalkene sulfonates or mixtures thereof having 12 to 16 carbon atoms in the carbon chain of the molecule; and water soluble soaps of higher fatty acids, such as those of 12 to 18 carbon atoms, e.g., coconut fatty acids.

Examples of suitable nonionic surfactants for use in the second component of the present invention include condensates of sorbitan esters of fatty acids with ethylene oxide (polysorbates) such as sorbitan mono-oleate with from about 20 to about 60 moles of ethylene oxide. A particularly preferred polysorbate is Polysorbate 20, polyoxyethylene 20 sorbitan monolaurate, marketed by ICI, Newcastle, Del. 19720.

Additional suitable nonionic surfactants useful in the second component of the present invention are the condensation products of an alpha-olefin oxide containing 10 to 20 carbon atoms, a polyhydric alcohol containing 2 to 10 carbon atoms and 2 to 6 hydroxyl groups, and either ethylene oxide or a mixture of ethylene oxide and propylene oxide. The resultant surfactants are polymers which have a molecular weight in the range from about 400 to about 1600, contain from about 40% to about 80% ethylene oxide, by weight, and have an alpha-olefin oxide to polyhydric alcohol mole ratio in the range from about 1:1 to about 1:3, respectively. Other nonionic surfactants useful in the present invention include condensates of sorbitan esters of fatty acids with polyethylene glycol such as sorbitan diisostearate condensed with polyethylene glycol.

The surface active agent can be present in one or both components of the compositions of the present invention, at a concentration of about 0.1 to about 5.0% by weight, preferably about 0.2 to about 1.5% by weight of the particular component.

Siliceous abrasive materials useful in the practice of the invention include, preferred silicas which have a mean particle size up to about 20 microns; including a precipitated amorphous hydrated silica, such as Zeodent 115, marketed by J. M. Huber Chemicals Division, Havre de Grace, Md. 21078, or Sylodent 783 marketed by Grace Davidson, Baltimore, Md. 21203.

The silica abrasive is present in each of the two dentifrice components of the present invention at a concentration from about 5 to about 30% by weight, and preferably about 5 to about 20% by weight of the respective component.

Fluoride Source Containing Component

The first component of the dentifrice composition of the present invention contains sodium fluoride, as the source of fluoride ions. The sodium fluoride is incorporated in the first component at a concentration of about 0.1 to about 3.0% by weight, and preferably at about 2.0 to about 2.5% by weight. At these preferred concentrations, about 4,500 ppm to over 5,600 ppm, fluoride ion will be available in solution, when the combined first and second components of the dentifrice composition are admixed and applied to the teeth.

It is also critical to the practice of the present invention that the first component be maintained at a pH of at least about 7.5, and preferably at a pH of at least about 8.0. Applicants' have discovered that NaF is stable in the presence of the siliceous abrasive only in a neutral or basic pH environment. A buffering agent, such as sodium hydroxide and sodium bicarbonate or sodium phosphate may be employed to adjust the pH of the fluoride ion containing dentifrice component to the desired basic levels, if necessary.

Acid Containing Component

The second component of the dentifrice composition of the present invention, which is maintained physically separate from the first component until mixing before use, contains an acid or mixture of acids, to acidulate the dentifrice when the two components are mixed prior to use. Acidic compounds which can be present in the second component include both mineral and organic acids, such as, sulfuric acid, hydrochloric acid, malic acid, alginic acid, citric acid, succinic acid, lactic acid, tartaric acid, potassium bitartrate, acid sodium citrate, phosphoric acid, and sodium acid phosphate. Acid phosphates are preferred, including phosphoric acid, or salts of phosphoric acid containing the radical $PO_4$, as such acids or acid salts thereof, such as sodium phosphate monobasic, not only provide the necessary acidity; but, also provide phosphate ions, to inhibit any tooth enamel demineralization which may occur with the application of the two component acidulated dentifrice to the teeth. Further, the combination of an acid such as phosphoric acid and an acid salt, such as sodium phosphate monobasic, provides enhanced buffering to achieve the desired pH upon the mixing of the dentifrice components. The preferred acid, phosphoric acid is commercially available as a liquid at 85% concentration and the preferred sodium phosphate monobasic is commercially available as a monohydrate powder.

The acid is incorporated in the second component of the dentifrice composition of the present invention in a total concentration of about 0.7% to about 4% by weight and preferably at about 2.0 to about 3.0% by weight; the amount being sufficient to obtain a pH of from about 2.5 to about 5.0 and preferably from about 3.5 to about 4.5.

The concentration of phosphate ions within the second component of the present invention is at least about 0.05 M, with a concentration of at least about 0.2 M preferred.

Other Ingredients Common to Both Components

Inorganic or organic thickeners may be included in the both of the components of the dentifrice of the present invention. Organic thickeners such as, natural and synthetic gums and colloids may also be incorporated in the present invention. Examples of such organic thickeners include carrageenan (Irish moss), xanthan gum and sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. Inorganic thickeners include amorphous silica compounds which function as thickening agents, such as colloidal silicas compounds available under tradenames such as Cab-o-sil fumed silica manufactured by Cabot Corporation and distributed by Lenape Chemical, Bound Brook, N.J., Zeodent 165 from J. M. Huber Chemicals Division, Havre de Grace, Md. 21078, and Sylox 15 from Grace Davidson, Baltimore, Md. 21203. A combination of inorganic and organic thickening agents are preferred and may be present in both components of the instant dentifrice in proportions of about 0.5 to about 15% by weight, preferably about 0.8 to about 6% in each of the two dentifrice components.

A striped dentifrice product may be obtained using the multicomponent dentifrice of the present invention, wherein colorants of contrasting colors are incorporated in each of the dentifrice components to be dispensed; the colorants being non-toxic when used in the suggested amounts. Colorants used in the practice of the present invention include both pigments and dyes.

Pigments used in the practice of the present invention include non-toxic, water insoluble inorganic pigments such as titanium dioxide ($TiO_2$) and chromium oxide greens, ultramarine blues and pinks and ferric oxides. Dyes include water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The concentration of the pigment or dye in the dentifrice composition ranges in amount from about 0.0005 percent to about 2 percent by weight of the respective component.

Other ingredients which may be incorporated in one or both components of the present invention, include antibacterial agents, antitartar actives, sweetener, flavor and preservatives, such as sodium benzoate.

Preferred antibacterial agents are non-cationic antibacterial agents based on phenolic and bisphenolic compounds, halogenated diphenyl ethers such as triclosan, benzoate esters and carbanilides. Cationic antibacterial agents which are also preferred, including quaternary ammonium salts, such as, chlorhexidine digluconate; can only be included in the second acid containing component of the present invention. Such antibacterial agents can be present in quantities of from about 0.03 to about 1% by weight of the particular component.

Antitartar actives such as sodium tripolyphosphate, tetrapotassium or tetrasodium pyrophosphates, or mixtures thereof, can be present in concentrations from about 0.5 to about 8% by weight of the particular component in which such actives are stable. The sweetener content will normally be that of an artificial or synthetic sweetener and the normal proportion thereof present will be in the range of 0.1 to 1% by weight of the respective component, preferably 0.2 to 0.5% by weight the respective component. The flavor content, which is preferably a fruit or mixed peppermint/menthol flavor, will usually be in the range of 0.5 to 2% by weight of the respective component, preferably 0.5 to 1.0% by weight of the respective component. The contents of other components or adjuvants will normally not exceed 10% by weight, often will be less than 5% by weight, and can be as low as 0%.

When noncationic antibacterial agents are included in any of the dentifrice components, there is also preferably included from about 0.05 to about 5% of an antibacterial enhancing agent (AEA) which enhances the delivery and retention of the noncationic antibacterial agent to, and retention thereof on oral surfaces. AEA's useful in the present invention are disclosed in U.S. Pat. Nos. 5,188,821 and 5,192,531; and include synthetic anionic polymeric polycarboxylates, in the form 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez, e.g. AN 139 (M.W. 500,000), AN 119 (M.W. 250,000) and preferably S-97 Pharmaceutical Grade (M.W. 700,000) available from ISP Technologies, Inc., Bound Brook, N.J. 08805.

Preparation of the Dentifrice

To prepare either of the dentifrice components of the present invention, generally the humectants e.g. glycerin, propylene glycol, polyethylene glycol ingredients, are dispersed with any sweetener and water in a conventional mixer, until the mixture becomes a homogeneous gel phase. Into the gel phase are added a pigment such as $TiO_2$, any antibacterial agent such as triclosan, any antibacterial enhancing agent such as Gantrez, any tartar control agents such as tetrasodium pyrophosphate or sodium tripolyphosphate or both, in the second component the acid phosphate, and in the first component the fluoride ion source, i.e. sodium fluoride. These ingredients are mixed until a homogenous phase is obtained. Thereafter the thickener, silica abrasive, flavor and surfactant ingredients are added and the ingredients mixed at high speed under vacuum of from about 20 to 100 mm of Hg. The resultant product is in the case of each component is a homogeneous, semi-solid, extrudable paste product.

Packaging of the Dentifrice

The multicomponent dentifrice composition of the present invention is packaged in a suitable dispensing container in which the components are maintained physically separated and from which the separated components may be dispensed synchronously as a ribbon for application to a toothbrush. Such containers are known in the art. An example of such a container is a two compartment dispensing container, such as a pump or tube, having collapsible sidewalls, as disclosed in U.S. Pat. Nos. 4,487,757 and 4,687,663; wherein, the container body is formed from a collapsible plastic web and is provided with a partition within the container body defining separate compartments in which the physically separated components are stored and from which they are dispensed through a suitable dispensing outlet.

The following example is further illustrative the present invention, but it is understood that the invention is not limited thereto. All amounts and proportions referred to herein and in the appended claims are by weight, unless otherwise stated.

EXAMPLE

A two component dentifrice of the present invention was prepared, designated Toothpaste I, having a first sodium fluoride and silica abrasive containing component and a second acid phosphate and silica abrasive containing component. The ingredients and pH of each of the two components of Toothpaste I are itemized in Table I, below.

TABLE I

Toothpaste I

| Ingredients | 1st Component (in weight %) | 2nd Component (in weight %) |
|---|---|---|
| PEG 600 | 3.00 | 3.00 |
| Xanthan Gum | 0.80 | 0.80 |
| Sorbitol | 37.15 | 36.58 |
| Water | 39.24 | 38.24 |
| Sodium fluoride* | 2.21 | — |
| Sodium benzoate | 0.50 | 0.50 |
| Phosphoric Acid 85% | — | 0.96 |
| Sodium phosphate monobasic | — | 1.82 |
| Sodium saccharin | 0.25 | 0.25 |
| Dye | 0.50 | 0.50 |
| Sylox 15 | 10.0 | 10.0 |
| Zeodent 115 | 5.35 | 5.35 |
| Polysorbate 20 | — | 0.50 |
| Sodium Lauryl Sulfate | 1.0 | — |
| Flavor | 0.50 | 0.50 |
| Total % | 100% | 100% |
| pH | 8.0 | 3.5 |

*Contains potentially 5000 ppm releasable F− with combination of 1st and 2nd components upon admixing prior to application to the dentiture.

To determine the fluoride ion availability of the multi-component dentifrice of the present invention, after storage for a period of 8 weeks, the $1^{st}$ and $2^{nd}$ components of Toothpaste I were mixed together, diluted one-thousand times using a commercially available buffering solution (Orion TISAB II), at ambient room temperature; the available fluoride ion concentration was determined using a Corning Model 350 pH/ion Analyzer, Corning Inc., Corning N.Y., equipped with a Orion Fluoride Electrode, Model #94-09, Orion Research Products, Boston, Mass. The EMF output from the Orion Fluoride Electrode was converted to ppm fluoride by means of a logarithmic-linear calibration established with known concentrations of fluoride in the buffering solution and the resultant ppm of available fluoride determined has been recorded in Table III, below.

For purposes of comparison, the procedure was repeated except the dentifrice assayed for fluoride availability was a single component acidulated phosphate fluoride dentifrice of the prior art, containing a silica abrasive designated, Toothpaste II, having the ingredients and pH listed in Table II, below. Referring to Table II, note that the amount of sodium fluoride within Toothpaste II is one-half that of the $1^{st}$ Component of Toothpaste I, so that a comparable potential 5,000 ppm of fluoride would be delivered upon use by each. After a comparable eight weeks of storage, the available soluble fluoride of Toothpaste II was assayed using the same methodology as that used for Toothpaste I and the results are also recorded in Table III, below.

TABLE II

Toothpaste II

| Ingredients | Composition (in weight %) |
|---|---|
| PEG 600 | 3.00 |
| Xanthan Gum | 0.80 |
| Sorbitol | 34.37 |
| Water | 39.345 |
| Sodium fluoride | 1.105 |
| Sodium benzoate | 0.50 |
| Phosphoric Acid 85% | 0.96 |
| Sodium phosphate monobasic | 1.82 |
| Sodium saccharin | 0.25 |
| Dye | 0.50 |
| Sylox 15 | 10.0 |
| Zeodent 115 | 5.35 |
| Polysorbate 20 | 0.50 |
| Sodium Lauryl Sulfate | 1.0 |
| Flavor | 0.50 |
| Total % | 100% |
| pH | 5.0 |

TABLE III

Fluoride Availability

| Toothpaste Analyzed | Available Soluble Fluoride Ion (in ppm) |
|---|---|
| Toothpaste I | 4,900 |
| Toothpaste II | 3,800 |

Referring to Table III, the 4,900 ppm is equivalent to 98% availability of the fluoride in Toothpaste I and the 3,800 ppm is correspondingly equivalent to 76% fluoride availability in Toothpaste II. The 22% difference in available fluoride between Toothpaste I of the present invention and comparative Toothpaste II is significant and unexpectedly large. The magnitude of the loss of available fluoride in Toothpaste II is at a level of significance rendering Toothpaste II commercially unacceptable.

What is claimed is:

1. A method for the fluoridation of teeth utilizing a two component dentifrice system which is free of any water soluble calcium salts comprising the steps of (1) preparing a first dentifrice component containing from about 2.0% to about 2.5% by weight sodium fluoride as the fluoridation source and having a pH of at least about 7.5, and a second fluoride free, dentifrice component containing a source of phosphate ions and an acid in an amount sufficient to maintain the pH in the range of about 2.5 to about 5.0; both dentifrice components containing a siliceous abrasive; (2) maintaining the first and second dentifrice components separate from the other until application to teeth requiring fluoridation; (3) mixing the first and second components together to form a mixture having a pH of from about 4.0 to about 6.0, (4) applying the mixture to the teeth, whereby enhanced availability of fluoride ions to tooth enamel is observed.

2. The method of claim 1, wherein the source of phosphate ions is phosphoric acid, sodium phosphate monobasic or a combination thereof.

3. The method of claim 1, wherein the first component contains from about 0.1 to about 3.0% by weight sodium fluoride.

4. The method of claim 1, wherein the second component contains from about 0.7 to about 4% by weight of an acid phosphate and an acid salt.

5. The method of claim 4, wherein the acid phosphate is phosphoric acid and the acid salt is sodium phosphate monobasic.

6. The method of claim 1, wherein the pH of the first component is at least about pH 8.0.

7. The method of claim 1, wherein the acid is in an amount sufficient to maintain the pH of the second component in the range of about pH 3.5 to about pH 4.5.

8. The method of claim 1, wherein the siliceous abrasive is a precipitated amorphous hydrated silica.

9. The method of claim 8, wherein the dentifrice composition contains from 10 to 30% in total of the amorphous hydrated silica abrasive.

10. The method of claim 9, wherein both components of the dentifrice system each contain 15.35% by weight of the amorphous hydrated silica abrasive.

11. The method of claim 1, wherein a surfactant is incorporated in both components of the dentifrice system.

12. The method of claim 11, wherein the surfactant incorporated in the first component of the dentifrice system is sodium lauryl sulfate and the surfactant incorporated in the second component of the dentifrice is a condensate of sorbitan esters of fatty acids with ethylene oxide.

* * * * *